US010463290B2

(12) United States Patent
Hopper

(10) Patent No.: US 10,463,290 B2
(45) Date of Patent: Nov. 5, 2019

(54) BIOLOGICAL SAMPLE COLLECTION AND STORAGE ASSEMBLY

(71) Applicant: AXXIN PTY LTD, Fairfield (AU)

(72) Inventor: William R. Hopper, Fairfield (AU)

(73) Assignee: Axxin Pty Ltd., Fairfield (AU)

( * ) Notice: Subject to any disclaimer, the term of this patent is extended or adjusted under 35 U.S.C. 154(b) by 16 days.

(21) Appl. No.: 15/526,446

(22) PCT Filed: Nov. 13, 2015

(86) PCT No.: PCT/AU2015/050715
§ 371 (c)(1),
(2) Date: May 12, 2017

(87) PCT Pub. No.: WO2016/074046
PCT Pub. Date: May 19, 2016

(65) Prior Publication Data
US 2017/0318802 A1 Nov. 9, 2017

(30) Foreign Application Priority Data

Nov. 14, 2014 (AU) ................... 2014904586

(51) Int. Cl.
*A61B 5/15* (2006.01)
*G01N 1/02* (2006.01)
(Continued)

(52) U.S. Cl.
CPC ...... *A61B 5/150267* (2013.01); *A01N 1/0231* (2013.01); *A01N 1/0263* (2013.01);
(Continued)

(58) Field of Classification Search
CPC ............... G01N 33/48; G01N 33/4875; G01N 33/48778; G01N 33/49; G01N 33/491;
(Continued)

(56) References Cited

U.S. PATENT DOCUMENTS 4,234,540 A  11/1980 Ginsberg et al.
4,250,266 A  2/1981 Wade
(Continued)

FOREIGN PATENT DOCUMENTS

AU  2013202899 A1  5/2013
EP  1059523 B1  7/2007
(Continued)

OTHER PUBLICATIONS

Cikos et al.; Transformation of real-time PCR fluorescence data to target gene quantity; Analytical Biochemistry; 384(1); pp. 1-10; Jan. 1, 2009.
(Continued)

*Primary Examiner* — Benjamin R Schmitt
(74) *Attorney, Agent, or Firm* — Shay Glenn LLP

(57) ABSTRACT

A biological sample collection and storage assembly, including: at least one filtering component; and an absorbent storage component; wherein the at least one filtering component is configured to filter a received biological sample in fluid form containing free cells and other biological components to separate the free cells from the other biological components such that the other biological components flow to the absorbent storage component for subsequent testing or analysis.

20 Claims, 11 Drawing Sheets

View A-A

(51) Int. Cl.
*A01N 1/02* (2006.01)
*G01N 1/00* (2006.01)
*G01N 1/40* (2006.01)

(52) U.S. Cl.
CPC ......... *A61B 5/150358* (2013.01); *G01N 1/02* (2013.01); *G01N 2001/005* (2013.01); *G01N 2001/4088* (2013.01)

(58) Field of Classification Search
CPC ............... G01N 33/50; G01N 33/5005; G01N 2001/4088; G01N 2015/0065; A61B 5/15; A61B 5/150007; A61B 5/150053; A61B 5/150358; A61B 5/150267
USPC ...... 604/317, 358, 378, 403, 406; 73/864.72
See application file for complete search history.

(56) References Cited

U.S. PATENT DOCUMENTS

| | | | |
|---|---|---|---|
| 4,912,034 | A | 3/1990 | Kalra et al. |
| 5,152,965 | A | 10/1992 | Fisk et al. |
| 5,435,970 | A | 7/1995 | Mamenta et al. |
| 5,955,351 | A | 9/1999 | Gerdes et al. |
| 6,171,870 | B1 | 1/2001 | Freitag |
| 6,197,598 | B1 | 3/2001 | Schrier et al. |
| 8,895,296 | B2 | 11/2014 | Sano et al. |
| 2002/0031768 | A1 | 3/2002 | McMillan et al. |
| 2003/0129738 | A1 | 7/2003 | Sorenson et al. |
| 2003/0170686 | A1 | 9/2003 | Hoet et al. |
| 2004/0161788 | A1 | 8/2004 | Chen et al. |
| 2004/0265173 | A1 | 12/2004 | Matsumoto et al. |
| 2005/0033196 | A1* | 2/2005 | Alroy ............... A61B 5/150022 600/573 |
| 2005/0142031 | A1 | 6/2005 | Wickstead et al. |
| 2005/0180891 | A1 | 8/2005 | Webster et al. |
| 2006/0030790 | A1* | 2/2006 | Braig ................ A61B 5/14532 600/584 |
| 2006/0188392 | A1 | 8/2006 | Tanaka et al. |
| 2006/0223172 | A1 | 10/2006 | Bedingham et al. |
| 2006/0270027 | A1 | 11/2006 | Shaw et al. |
| 2006/0275852 | A1 | 12/2006 | Montagu et al. |
| 2006/0275922 | A1 | 12/2006 | Gould et al. |
| 2006/0292035 | A1 | 12/2006 | Gould et al. |
| 2007/0184492 | A1 | 8/2007 | Wang et al. |
| 2008/0020380 | A1 | 1/2008 | Patno et al. |
| 2008/0166820 | A1 | 7/2008 | Gould et al. |
| 2008/0199851 | A1 | 8/2008 | Egan et al. |
| 2008/0287308 | A1 | 11/2008 | Hubbell et al. |
| 2009/0181388 | A1 | 7/2009 | You et al. |
| 2009/0204997 | A1 | 8/2009 | Xu et al. |
| 2011/0039261 | A1 | 2/2011 | Hillebrand et al. |
| 2011/0283818 | A1 | 11/2011 | Kramer |
| 2012/0076693 | A1 | 3/2012 | Hopper |
| 2013/0309679 | A1 | 11/2013 | Ismagilov et al. |
| 2014/0194305 | A1 | 7/2014 | Kayyem et al. |
| 2014/0377766 | A1 | 12/2014 | Hopper |
| 2015/0190805 | A1 | 7/2015 | Etheredge et al. |
| 2015/0203904 | A1 | 7/2015 | Hopper |

FOREIGN PATENT DOCUMENTS

| | | |
|---|---|---|
| EP | 2123360 A1 | 11/2009 |
| EP | 2163999 A2 | 3/2010 |
| JP | H08-43294 A | 2/1996 |
| WO | WO92/08986 A1 | 5/1992 |
| WO | WO99/57561 A2 | 11/1999 |
| WO | WO 2005/045408 A1 | 5/2005 |
| WO | WO 2006/047777 A2 | 5/2006 |
| WO | WO 2007/005077 A1 | 1/2007 |
| WO | WO2007/106579 A2 | 9/2007 |
| WO | WO 2008/005248 A2 | 1/2008 |
| WO | WO 2009/011869 A1 | 1/2009 |
| WO | WO 2009/132268 A1 | 10/2009 |
| WO | WO2010/030686 A1 | 3/2010 |
| WO | WO2010/104478 A1 | 9/2010 |
| WO | WO2013/113054 A1 | 8/2013 |
| WO | WO2014/000037 A1 | 1/2014 |
| WO | WO2014/100732 A1 | 6/2014 |
| WO | WO2015/084458 A2 | 6/2015 |

OTHER PUBLICATIONS

Durtschi et al.; Evaluation of quantification methods for real-time PCR minor groove binding hybridization probe assays; Analytical Biochemistry; 361(1); pp. 55-64; Jan. 4, 2007.
Gubala et al.; Point of care diagnostics: status and future; Analytical Chemistry; 84(2); pp. 487-515; Jan. 2012.
Liu et al.; Progress curve analysis of qRT-PCR reactions using the logistic growth equation; Biotechnology Progress; 27(5); pp. 1407-1414; Sep. 15, 2011.
Pipper et al.; Clockwork PCR including sample preparation; Angew. Chem. Int. Ed.; 47(21); pp. 3900-3904; Apr. 15, 2008.
Roche Diagnostics GMBH; LightCycler 480 Instrument Operator's Manual, Software version 1.5; © 2008; 8 pages; Oct. 15, 2014; retrieved from the Internet (http://pedrovale.files.wordpress.com/2013/08/lightcyclerc2ae-480-instrument-operators-manual.pdf).
Wikipedia; Immunoassay; 4 pages; Feb. 24, 2015; retrieved from the internet (http://en.wikiopedia.org/wiki/Immunoassay).
Wikipedia; Lateral flow test; 4 pages; Feb. 24, 2015; retrieved from the internet (http:en.wikipedia.org/wiki/Lateral_flow_test).
Wikipedia; Polymerase chain reaction; 13 pages; Oct. 15, 2014; retrieved from the internet (http://en.wikipedia.org/wiki/Polymerase_chain_reaction).
Wikipedia; Variants of PCR; 11 pages; Oct. 15, 2014; retrieved from the internet (http://en.wikipedia.org/wiki/Variants_of_PCR#Isothermal_amplification_methods).
European Leukemia Network; Imatinib testing for CML; 7 pages; retrieved from the internet (https://www.eutos.org/content/molecular_monitoring/information/pcr_testing/index_eng.html); on Apr. 4, 2018.
Zhang et al.; Micropumps, microvalves, and micromixers within pcr microfludic chips: Advances and trends; Biotechnology Advances; 25(5); pp. 483-514; Sep. 1, 2007.
Hopper; U.S. Appl. No. 15/742,048 entitled "Diagnostic test assembly, apparatus, method," filed Jan. 5, 2018.

* cited by examiner

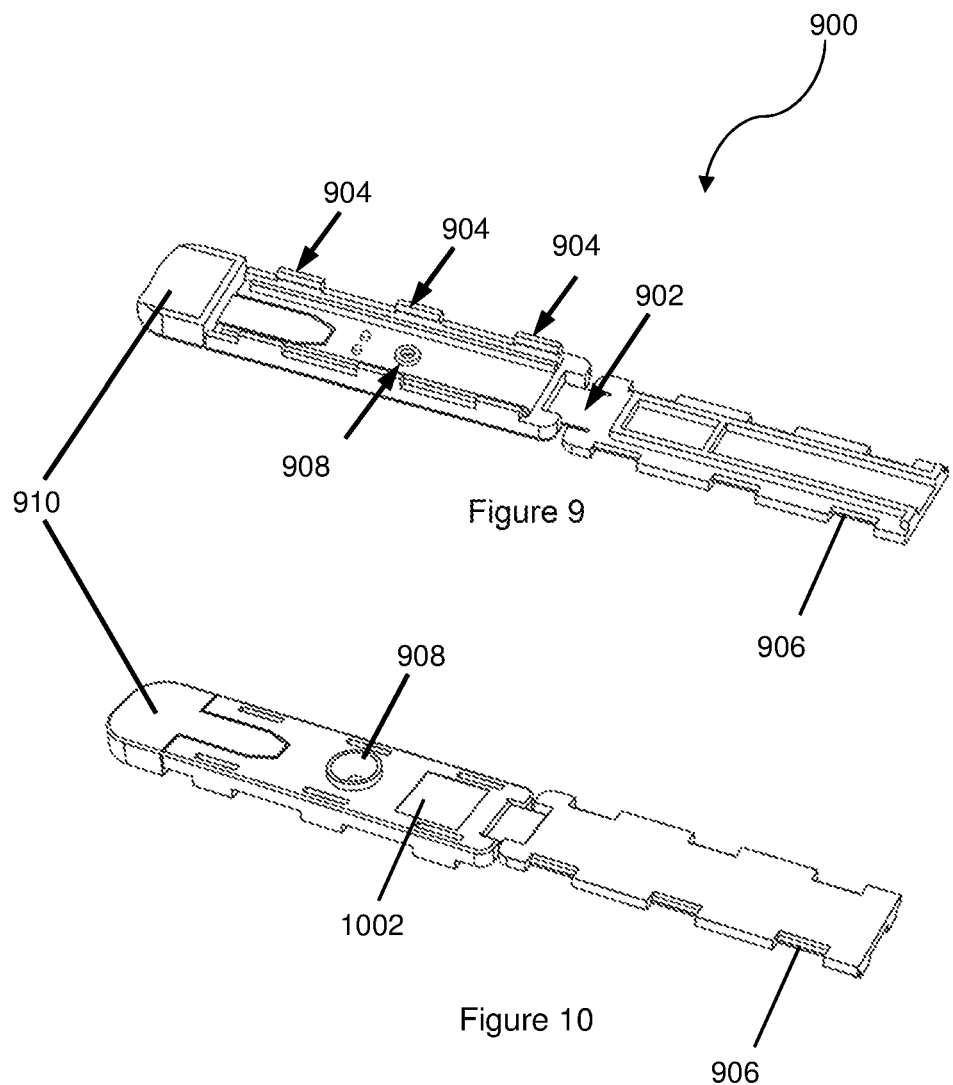

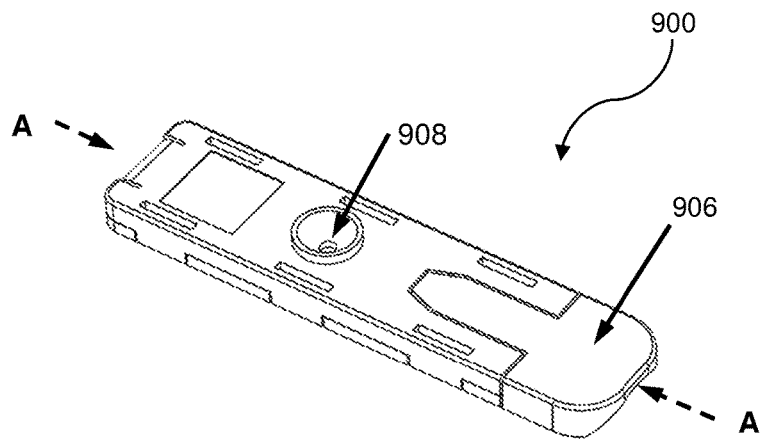
Figure 11
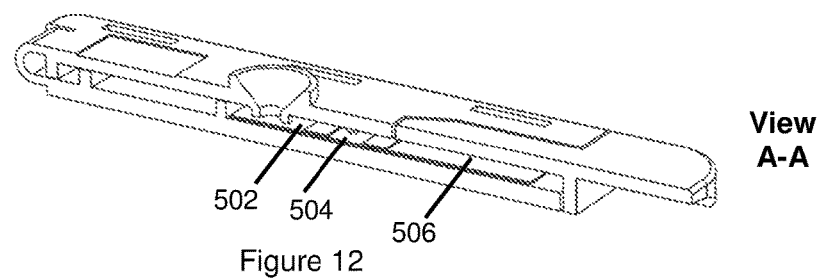
View A-A
Figure 12
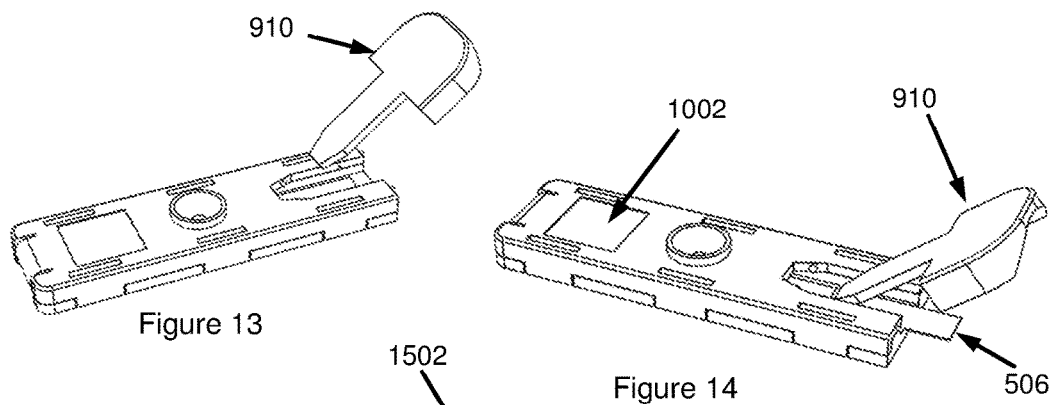
Figure 13
Figure 14
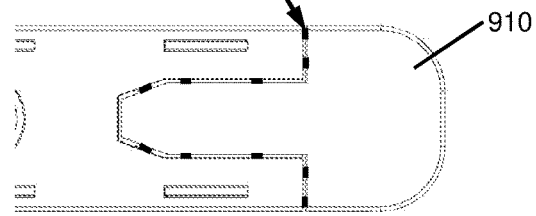
Figure 15

View A-A

BIOLOGICAL SAMPLE COLLECTION AND STORAGE ASSEMBLY

TECHNICAL FIELD

The present invention relates to a biological sample collection and storage assembly that allows a biological sample to be acquired, filtered, and stored for subsequent testing or analysis.

BACKGROUND

There is often a need to acquire biological samples in one location, and then transport them for testing or analysis at a second (and possibly very remote) location. The samples may need to be securely isolated from their environment (to protect against possible contamination of the sample by the environment, and vice versa), and in some cases the sample, once received at the second location, may not be in a convenient form for testing or analysis.

It is desired to provide a biological sample collection and storage assembly that alleviates one or more difficulties of the prior art, or that at least provides a useful alternative.

SUMMARY

In accordance with some embodiments of the present invention, there is provided a biological sample collection and storage assembly, including:
  at least one filtering component; and
  an absorbent storage component;
    wherein the at least one filtering component is configured to filter a received biological sample in fluid form containing free cells and other biological components to separate the free cells from the other biological components such that the other biological components flow to the absorbent storage component for subsequent testing or analysis.

In some embodiments, the at least one filtering component includes one or more selective chemical or immunoassay binding components to immobilise the free cells.

In some embodiments, the at least one filtering component uses size exclusion to restrict or block the passage of the free cells.

In some embodiments, a sample receiving component to receive the biological sample in fluid form, wherein the at least one filtering component is disposed between the sample receiving component and the absorbent storage component, and the biological sample flows from the sample receiving component to the absorbent storage component by capillary action.

In some embodiments, the sample receiving component, the filtering component, and the absorbent storage component are formed from a single material.

In some embodiments, one or more of the components are formed by selective thermal and/or mechanical processing of respective regions of the material.

In some embodiments, the assembly is configured to facilitate selective removal of the absorbent storage component for subsequent testing or diagnostic use of the other biological components stored therein.

In some embodiments, the filtering and storage components partially overlap such that a flow of fluid from a first of the components to an adjacent second one of the components occurs by capillary flow through an overlapping portion of the first component to a corresponding overlapping portion of the second component.

In some embodiments, the assembly includes a weakened or perforated region that facilitates selective removal of the absorbent storage component from the assembly for subsequent testing or diagnostic use of the other biological components stored therein.

In some embodiments, the assembly includes a weakened or perforated region that facilitates selective removal of the absorbent storage component from the assembly for subsequent testing or diagnostic use of the other biological components stored therein.

In some embodiments, the components partially overlap such that a flow of fluid from a first of the components to an adjacent second one of the components occurs by capillary flow through the overlapping portion of the first component to the overlapping portion of the second component.

In some embodiments, the components are supported by a common non-absorbent backing layer, and the adhesion of the absorbent storage component to the backing layer is configured to facilitate selective removal of the absorbent storage component.

In some embodiments, the storage component includes a plurality of mutually spaced separation regions to facilitate the separation and removal of corresponding portions of the storage component.

In some embodiments, the filtering and storage components are collectively in the form of a lateral flow strip.

In some embodiments, the assembly includes a housing in which the lateral flow strip is disposed to protect the lateral flow strip from contamination, and to protect the external environment and users from contamination from the biological sample within the housing, the housing including a port to receive the biological sample.

In some embodiments, the housing includes a sample removal component that is operable by a user to provide access to the storage component disposed within the housing.

In some embodiments, the housing provides a sample removal component operable to selectively engage the storage component and separate it from the at least one filtering component, and to subsequently release it from the assembly for testing or analysis.

In some embodiments, the housing provides a paddle or tool to facilitate removal of the storage component from the assembly, and its placement into a test tube.

In some embodiments, the housing includes a removable portion and a retaining portion configured for mutual separation, the removable portion including a sample engagement component operable by a user to selectively engage and release the storage component, such that a user of the assembly can:
  (i) operate the sample engagement component to selectively engage the storage component and thus retain it within the removable portion of the housing;
  (ii) separate the removable portion of the housing from the retaining portion of the housing, whereby the storage component remains engaged and is thus retained within the removable portion of the housing and separated from the at least one filtering component which is retained within the retaining portion of the housing; and
  (iii) operate the sample engagement component to selectively release the storage component from the removable portion of the housing for testing or analysis.

In some embodiments, the assembly includes a sealed reservoir storing a buffer solution, and a buffer solution release component that is operable by a user to cause release of the buffer solution from the sealed reservoir onto the lateral flow strip after the biological sample to improve flow of the biological sample within the lateral flow strip.

In some embodiments, the buffer solution includes a visible or fluorescent dye to facilitate observation of the progress of the sample flow through the lateral flow strip, the successful use and completion of the assembly, and/or prior use of the assembly.

In some embodiments, the housing includes a viewing port or window that allows a user to assess progress or correct operation of the collected sample in one or more regions of the strip, or whether the assembly has been prior used.

In some embodiments, the viewing port or window includes a lens to facilitate the assessment.

In some embodiments, the assembly includes a capillary port to allow direct collection of the fluid biological sample into the housing and onto the lateral flow strip.

In some embodiments, the assembly includes a spring loaded lancet operable by a user to cause a finger prick and thereby provide a blood sample for receipt by the capillary port.

BRIEF DESCRIPTION OF THE DRAWINGS

Some embodiments of the present invention are hereinafter described, by way of example only, with reference to the accompanying drawings, wherein:

FIGS. 9 to 15 are drawings illustrating the structure and operation of a first form of housing in accordance with some embodiments of the present invention;

DETAILED DESCRIPTION

Overview & Applications

Figure 1:
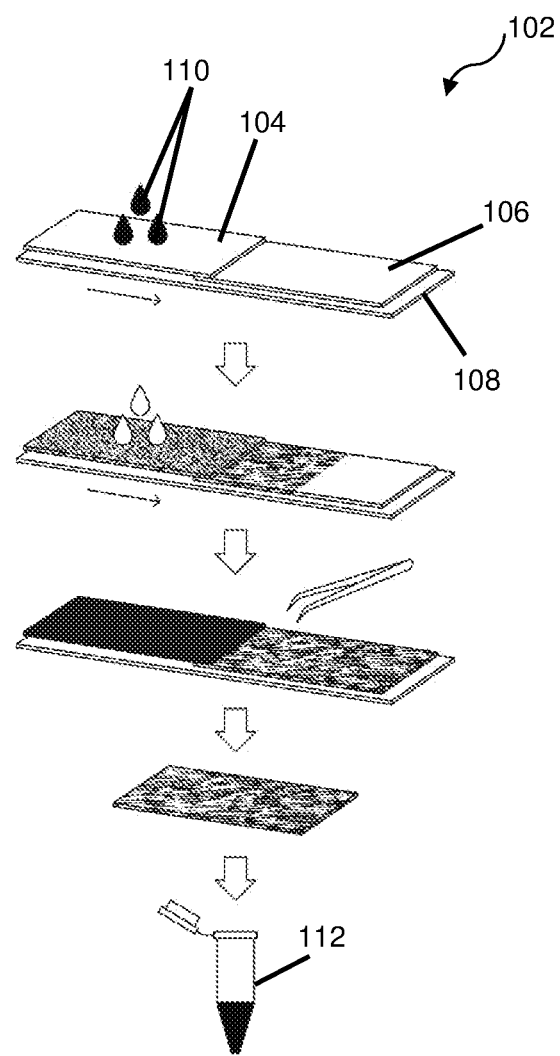
FIG. 1 is a drawing illustrating the steps involved in a typical use of a biological sample collection and storage assembly in accordance with the described embodiments of the present invention.

Described herein are biological sample collection and storage assemblies that allow a biological sample such as a blood sample to be captured, dried and preserved for subsequent testing or analysis. The described assemblies are particularly suited to the retention of RNA and DNA from biological samples, but are not limited to this application, and can also be used to acquire and retain for subsequent testing a wide range of other biological components, including protein, enzymes, and antibody markers, for example. Other biological components and applications of the described assemblies will be apparent to those skilled in the art in light of this disclosure.

Existing biological sample storage technologies such as Whatman paper are similar in some respects to the embodiments described herein to the extent that they also retain samples in an absorbent matrix and allow samples to dry for subsequent DNA testing. However, there is a particular limitation in these prior art approaches for storing biological samples that contain free cells (e.g., blood samples), because the whole biological sample is dried in place, and it is very difficult to separate out the free cells (e.g., blood cells) after the sample has dried.

Some tests cannot accept free cells, or are interfered with by the presence of free cells. For example, tests that use blood samples often specifically require blood plasma as the only sample medium, and consequently the red and white blood cells and other large particles must be removed to provide a blood plasma sample for testing. In a fresh blood sample, the plasma components are typically isolated by use of a centrifuge and subsequent removal of the separated plasma components for testing.

The biological sample collection and storage assemblies described herein address these difficulties by receiving a biological sample in fluid form, and filtering the biological sample to separate free cells and allow the filtered sample (i.e., with free cells removed) to flow out to an absorbent storage component or pad where it can be allowed to dry as a preservation method prior to subsequent testing. In the case of a blood sample, only the blood plasma will pass through to the storage component. The described assemblies also provide means to separate and remove the storage component containing the dried sample free of cells, such as blood plasma, for testing. Although some embodiments of the present invention are described herein in the context of blood samples, it should be understood that the invention has broader application to a wide range of different types of biological samples containing free cells, and is not limited to blood samples.

The biological sample collection and storage assemblies described herein include very low cost consumables that allow filtered blood plasma samples to be collected from patients. Blood plasma samples rapidly dry within the consumable, enabling the blood plasma samples to be safely and conveniently transported to a centralised laboratory for testing.

The described embodiments include a lateral flow strip assembly, which may be contained within a plastic housing to protect the strip assembly from contamination and allow transportation by essentially any transportation method, including a standard postal service, without requiring specialised handling procedures.

FIG. 1 is a schematic diagram illustrating the typical steps involved in using a biological sample collection and storage assembly in accordance with some embodiments of the present invention. As shown in the first (topmost) part of FIG. 1, a biological sample collection and storage assembly 102 includes a filtering component 104 and an absorbent storage component 106. In the described embodiments, these two components 104, 106 are mutually adjacent and in contact with one another, and are mounted on a common substrate or backing sheet 108.

A small amount (typically about 100 µl in volume) of a biological sample 110 (e.g., a blood sample) in fluid form and containing free cells and other biological components is received at the upper surface of the filtering component 104. The filtering component 104 is porous or absorbent, and the liquid sample 110 is drawn into the filtering component 104.

As shown in the second part of FIG. 1, a small amount (e.g., 2 to 3 drops) of a buffer solution may be added to the upper surface of the filtering component 104 in order to improve the flow of the biological sample 110.

The filtering component 104 is configured to filter the biological sample to separate the free cells from the other biological components such that the other biological components flow through the filtering component 104 to the absorbent storage component 106. In the case where the biological sample 110 is a blood sample, red blood cells are retained in the filtering component 104, which thereby becomes coloured red, whereas the storage component 106 receives only plasma components, and thereby becomes yellow coloured, as shown in the third part of FIG. 1. The storage component 106 is then left to dry, preserving and storing the plasma components for subsequent testing or analysis.

As shown in the fourth part of FIG. 1, the storage component 106 is then removed from the assembly 102, thus providing a convenient medium that stores only the components of the biological sample 110 that were not filtered from the fluid sample by the filtering component 104. In this form, the storage component 106 can be stored for subsequent testing or analysis, and if necessary can be shipped to a remote location for such testing.

Once received at a testing or analysis facility, the biological components stored in the storage component 106 can be tested or analysed by placing the storage component 106 (or a portion thereof) in a suitable test tube 112, as illustrated in the final part of FIG. 1.

A practical application of this technology is viral load monitoring, for example HIV viral load monitoring as a support diagnostic for clinical management of patients. In this example, a point of care (POC) test is not available, and testing in centralised health facility laboratories is required. This can make viral load testing challenging or unavailable in some regions, including resource-limited third world settings.

The assemblies described herein allow biological sample collection from patients in widely dispersed areas or large patient populations, and at low cost. Because free cells are removed from the acquired samples, the filtered samples can be allowed to dry on a preservation medium, and can be transported using low cost standard transport services without cold storage or special blood handling requirements. On arrival at a testing or diagnostic laboratory, the sample can then be used in subsequent tests, including molecular tests that detect the presence of specific RNA or DNA sequences.

Another potential application for this technology is general population and mass screening.

As described above, the biological sample collection and storage assemblies include a filtering component that removes free cells from a fluid biological sample. In some embodiments, as shown in the biological sample collection and storage assembly 200 of FIG. 2, the free cells are filtered chemically by including in the filtering component 202 one or more molecules (e.g., antibodies) that bind to the free cells and thereby prevent or at least impede their movement through the filtering component 202 to the storage component 204.

For example, in the case where the biological sample is a blood sample, the filtering component 202 can be treated with biological antibodies: for example, α-Glyc A to bind with red blood cells, and α-CD4 Ab to bind with CD4+ cells, so that only filtered blood plasma is able to flow laterally to the storage component 204.

Figure 2:
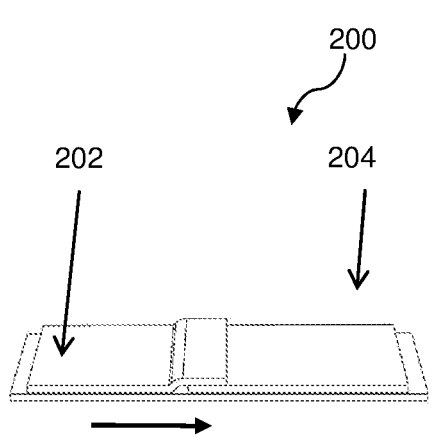
FIGS. 2 to 4 are drawings illustrating different assembly configurations for filtering cells from biological samples in accordance with the described embodiments of the present invention.
Figure 3:
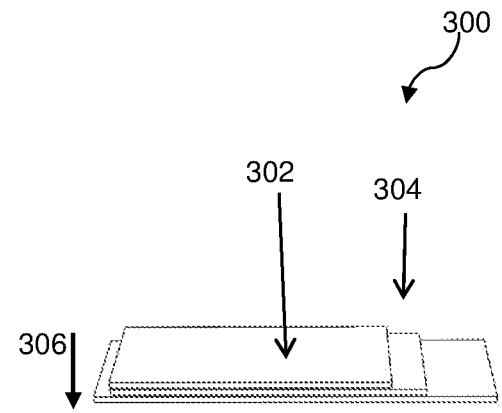

In some embodiments, as shown in the biological sample collection and storage assembly 300 of FIG. 3, the filtering of cells (and any other similarly large or larger entities) is achieved mechanically/physically, by providing a mesh, matrix or membrane 302 having openings no larger than a corresponding dimension of the entities to be filtered, thereby only allowing entities smaller than this dimension to pass through the mesh, matrix or membrane 302 to the storage component 304. This general method of mechanical filtering based on physical dimensions is also referred to herein as "size exclusion". As shown in FIG. 3, the filtering component or membrane 302 may be arranged above the storage component 304, so that the biological fluid flows in a vertical direction over a relatively short distance, as shown in FIG. 2, compared to the relatively long flow paths required when the flow is in a lateral direction through a sheet-like filtering component, for example, such as the assemblies 102, 200 of FIGS. 1 and 2.

Figure 4:
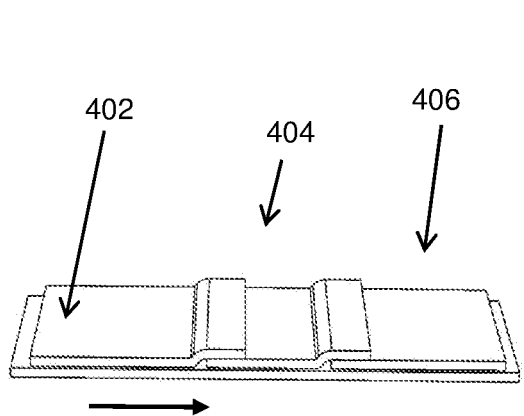

In the embodiments described below, a combination of chemical and physical filtering methods is used to filter cells from the biological fluid sample. As shown in the biological sample collection and storage assembly 400 of FIG. 4, these embodiments include a first filtering component 402 that incorporates α-Glyc A antibodies to filter red blood cells from the biological fluid sample, and a second filtering component 404 in the form of a membrane that physically/mechanically blocks the passage of white blood cells. These filtering components 402, 404 are arranged in serial fluid communication so that the corresponding component (or components) of the biological fluid needs to pass through both filtering components 402, 404 in order to reach the storage component or 'plasma collector 406. These embodiments rely on lateral flow by capillary action to draw the applied biological sample from the first filtering component 402 and through the second filtering component 404, allowing only the filtered blood plasma to flow to the absorbent storage component 406. As only a reasonably small sample of blood is applied, and it is distributed across a relatively large surface area of absorbent membrane, it rapidly dries in place.

It will be apparent that, where a fluid biological sample other than blood is to be processed, the (one or more) selective chemical or immunoassay binding components incorporated within any binding filtering component(s), and/or the physical dimensions of any physical (mesh, matrix or membrane) filtering components will be selected according to the chemical binding properties and/or physical dimensions of the corresponding components of the biological sample that are to be filtered from the sample as it flows to the storage component.

The absorbent membrane structure of the storage component 406 and its absorption of the filtered biological sample (e.g., blood plasma) ensures that, once dry, the sample is immobilised and secure for transport or long term storage prior to testing.

Although embodiments of the present invention are described herein in the context of the filtering components and storage component taking the general form of a conventional lateral flow strip, it will be apparent to those skilled in the art that either or both of the filtering and storage components may take other, different forms in other embodiments not specifically described herein.

However, an important advantage of arranging the filtering and storage components in the general form of a lateral flow strip is that the strip can be constructed using standard lateral flow manufacturing methods. These methods can include laying up strips of each strip component onto a backing card and then cutting the assembled card to form individual test strips.

The strips can also be manufactured using high speed web methods, where the strip components, including the filtering and storage components and substrate/backing strip, are supplied on reels and the material webs unwind from these reels in a mechanical assembly that controls the lateral position of the webs and laminates these into a continuous assembly on the backing sheet. The assembled web is then sliced into individual strips.

Cell Filtering Assembly

Figure 5:
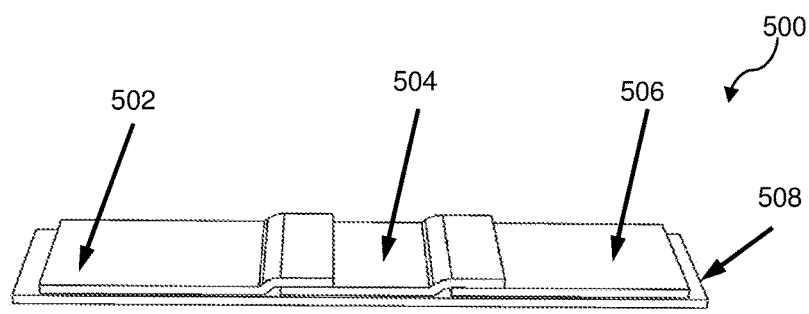
FIGS. 5 and 6 are drawings showing two views of a first form of a lateral flow strip assembly for filtering cells from a biological sample and storing the remaining biological components of the sample for subsequent testing or analysis.
Figure 6:
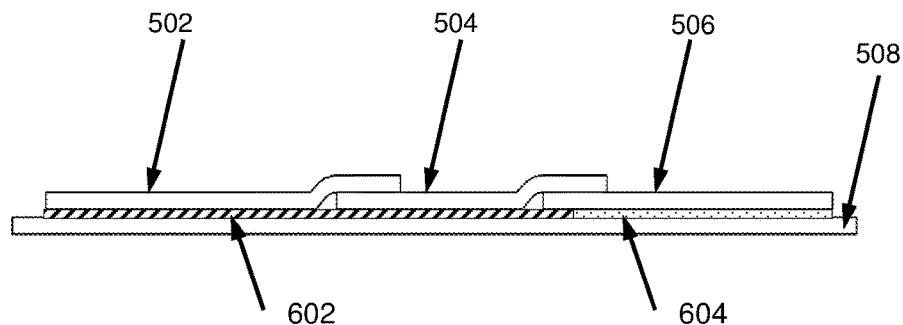

As shown in FIGS. 5 and 6, a biological sample collection and storage assembly or strip 500 includes a first filtering component 502, a second filtering component 504, and a storage component 506, arranged substantially in series to form a linear fluid flow device. These three components 502, 504, 506 are all formed from a standard absorbent, capillary flow material, and are typically mounted on a common, non-absorbent substrate or backing sheet 508 to facilitate handling. Depending on the choice of materials, the filtering and storage components 502, 504, 506 may be weakly bonded to the backing sheet 508 by natural contact adhesion only, or by use of an adhesive 602, as shown in FIG. 6.

To facilitate fluid flow from the first filtering component 502 to the second filtering component 504, and similarly from the second filtering component 504 to the absorbent storage component 506, these components 502, 504, 506 are arranged to partially overlap in pairs, such that a relatively small edge portion of each upstream component overlays a corresponding edge portion of the adjoining downstream component, thereby forming a step, generally similar to the standard arrangement of housing roof tiles. This arrangement provides a relatively large interface area between each pair of adjoining components.

The volume of biological fluid sample that the strip 500 can acquire and process can be selected as desired by corresponding selections of the sizes and/or compositions of the filtering and storage components 502, 504, 506 during manufacture.

Figure 7:
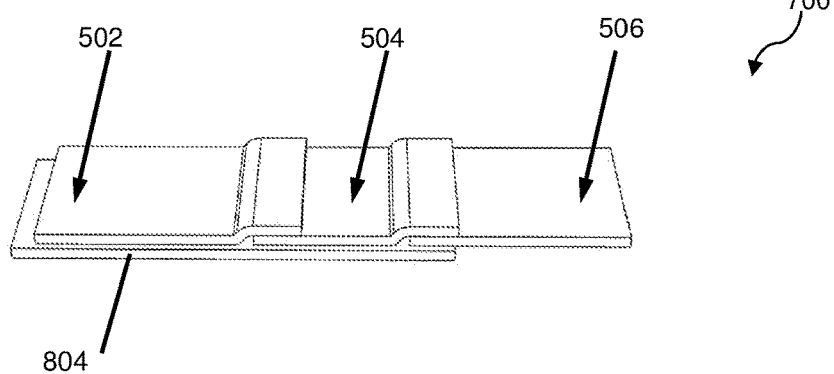
FIGS. 7 and 8 are drawings showing two views of a second form of a lateral flow strip assembly for filtering cells from a biological sample and storing the remaining biological components of the sample for subsequent testing or analysis.
Figure 8:
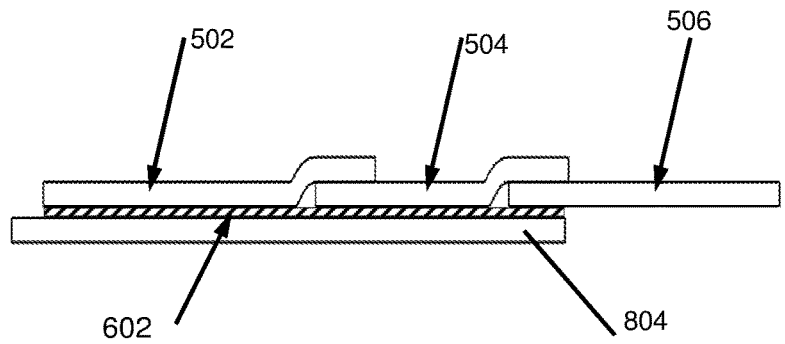
Figures 16, 17, 18, 19:
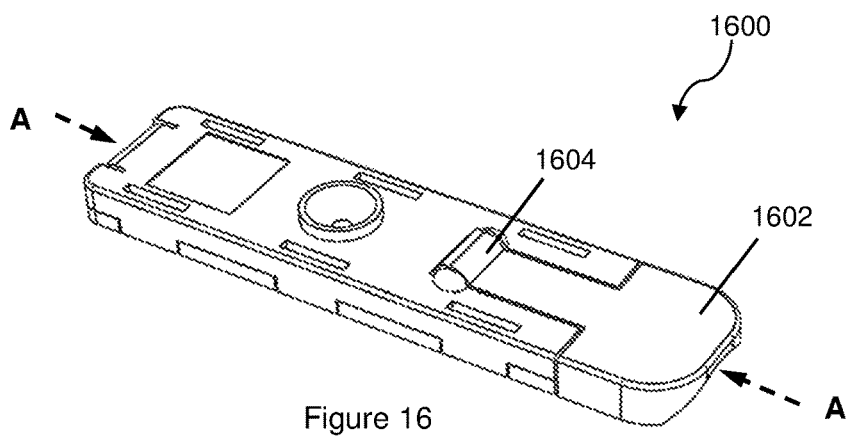
FIGS. 16 to 19 are drawings illustrating the structure and operation of a second form of housing in accordance with some embodiments of the present invention.
Figure 20:
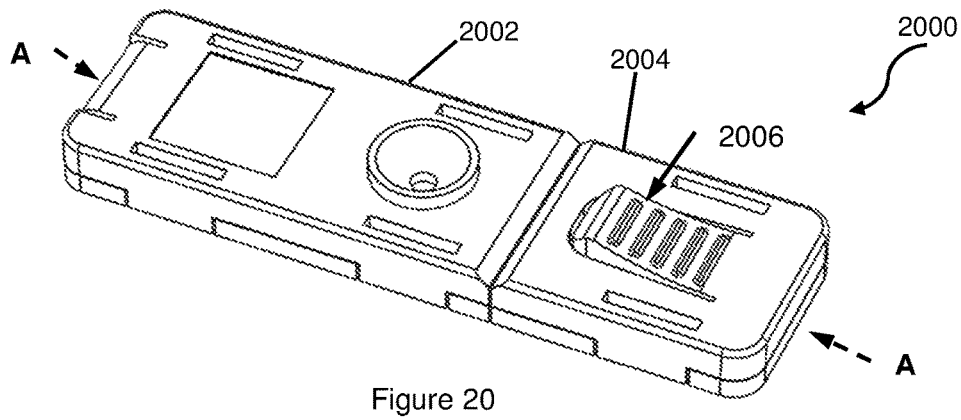
FIGS. 20 to 23 are drawings illustrating the structure and operation of a third form of housing in accordance with some embodiments of the present invention.
Figure 21:
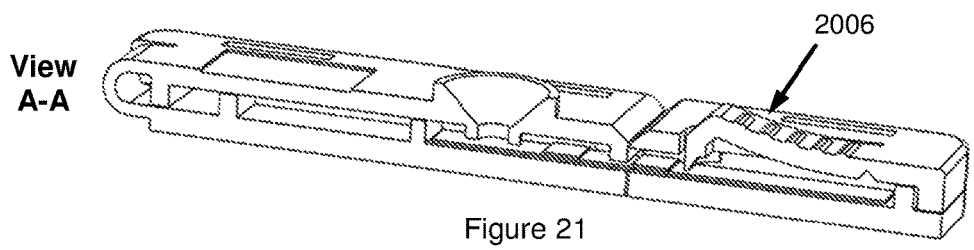
Figure 22:
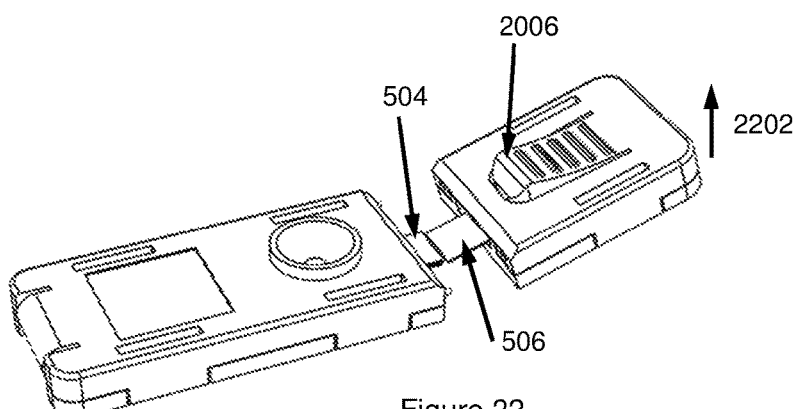
Figure 23:
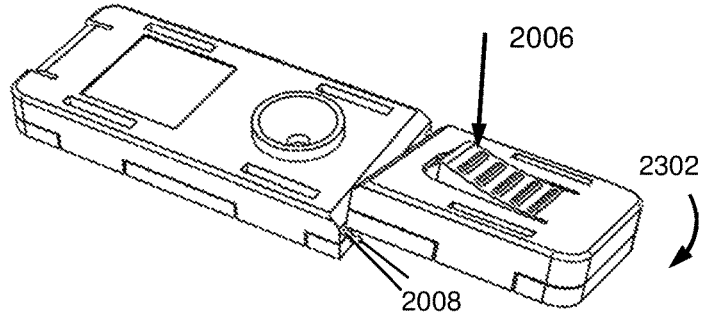
Figure 24:
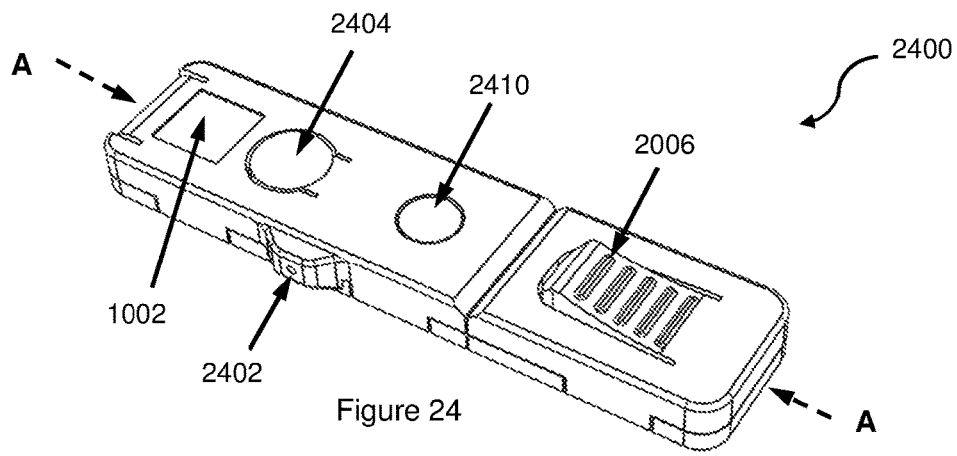
FIGS. 24 to 30 are drawings illustrating the structure and operation of a fourth form of housing in accordance with some embodiments of the present invention.
Figure 25:
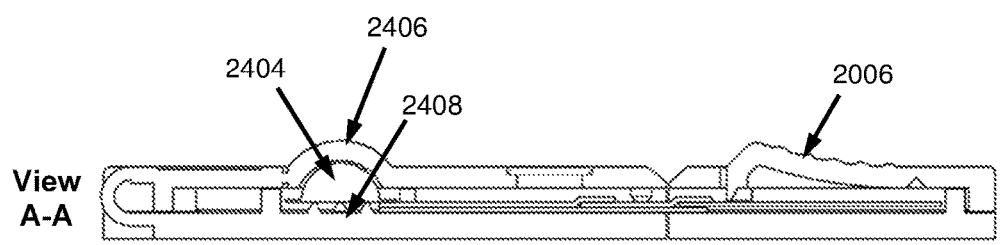
Figure 26:
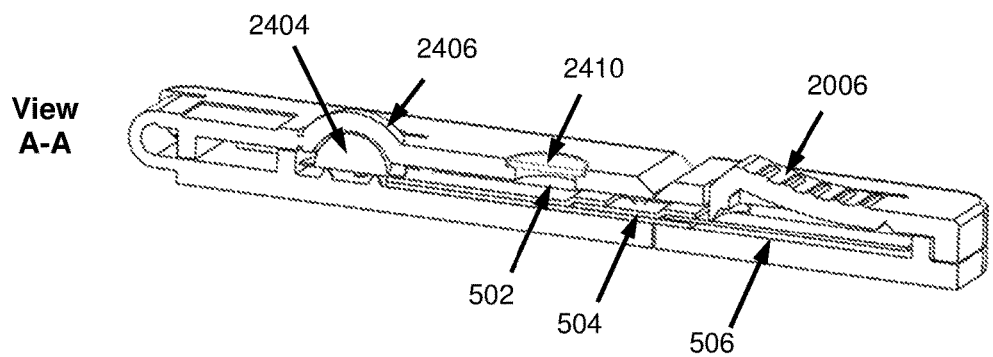
Figure 27:
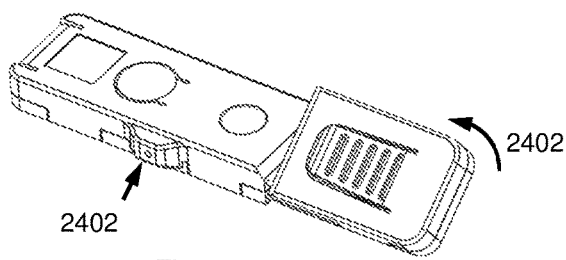
Figure 28:
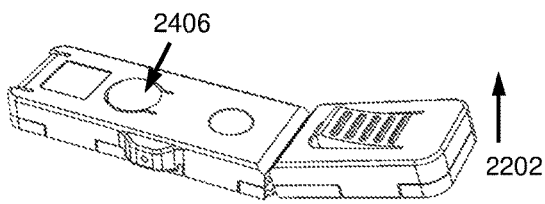
Figure 29:
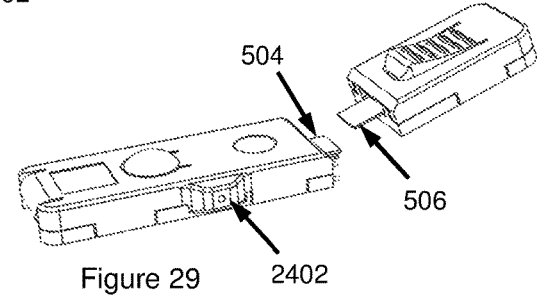
Figure 30:
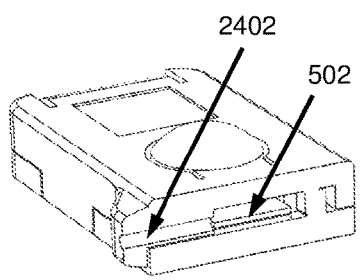

In the embodiment of FIGS. 5 and 6, a non-adhesive support material 604 is arranged under most of the storage component 506 to facilitate its removal during use, as described below. In this embodiment, only a small portion of the storage component 506 at or near the biological fluid-receiving end of the storage component 506 is supported and attached to the substrate 508 by the adhesive 602. In an alternative embodiment, as shown in the biological sample collection and storage assembly 700 of FIGS. 7 and 8, the major part of the storage component 506 (that in the embodiment of FIGS. 5 and 6 is supported by the non-adhesive support material 604) is completely unsupported in this embodiment 700 to facilitate subsequent removal of the storage component 506 (by omitting the support material 604 and using a shorter substrate or backing sheet 804). As will be appreciated by those skilled in the art, there are many other possible arrangements for facilitating the selective removal of the storage component 506 from the other components of the biological sample collection and storage assembly 700, and that will be apparent in light of this disclosure.

Assembly Housing

FIGS. 9 to 13 illustrate one form of housing or cartridge 900 in which a lateral flow strip assembly as described above is disposed to protect the strip from contamination, and, depending on the nature of the biological sample, also to protect the external environment and users from contamination from the biological sample stored within the housing 900.

For simplicity of description, the housings described below are described in the context of enclosing a three-component lateral flow strip assembly 500 of the form described above and shown in FIGS. 5 and 6. However, it should be understood that in general a lateral flow strip enclosed by a housing in accordance with embodiments of the present invention may be in any suitable form, including the lateral flow strip assemblies 200, 300, 400, 500, 700 described above and shown in FIGS. 2 to 8.

The housing 900 may be composed of a plastic, and in the general case can be assembled from one or more clip-together parts to enclose the lateral flow strip 500 therein. In the embodiment shown in FIGS. 9 to 13, the housing 900 takes the form of a single piece or moulding with a deformable hinge 902 between the two halves of the housing 900. To assemble the housing 900, the lateral flow strip 500 is placed on one of the two halves, and the other half is then folded over the first half to fully enclose the strip 500 between the two halves, which are then locked together. In the described embodiment, this is achieved by engagement of locking tabs 904 on one of the halves with corresponding ledges 906 on the other half. However, it will be apparent to those skilled in the art that other forms of engagement mechanism may be used to lock the two halves together in other embodiments.

The upper half of the housing includes a recessed region 1002 reserved for adding identification information to identify the specific sample and/or test. Typically, this information is provided on a given assembly by affixing to the recessed region 1002 an adhesive sticker or label with a two-dimensional QR-type barcode printed thereon.

The housing 900 also includes a sample port 908 and a sample access and removal component or tool 910. To use the biological sample collection and storage assembly of FIGS. 9 to 15, a biological sample in fluid form (described as blood in the following, but may be some other type of biological sample) is applied to the sample port 908. In the case of a finger prick blood sample, this sample transfer may use a separate moulded plastic single use sample capillary tube or bulb pipette. If required, a quantity of wash buffer or saline solution may also be added to wash the blood sample through the filtering component(s) 502, 504 of the strip 500.

Once applied to the sample port 908, the blood sample, under its own capillary action, flows through the filtering component(s) 502, 504, which in the general case filter free cells from the sample by binding reaction, or by size exclusion, or by a combination of both of these methods. The filtered sample, or plasma in the case of a blood sample, then flows out to the storage component 506 of the lateral flow strip 500.

As noted above, a wash buffer solution such as a saline solution may be specified or supplied and added to the sample port 908 after the biological sample. This wash buffer assists in driving the sample components fully through the filtering component(s) 502, 504, and thereby improves the performance of the assembly 500 in collecting the filtered components of the biological sample in the storage component 506.

In some embodiments, the housing includes a sample access component that is operable by a user to provide access to the storage component 506 disposed within the housing. In some embodiments, the housing provides a sample removal paddle or tool to facilitate removal of the storage component 506 from the assembly, and its placement into a test tube.

In the embodiment 900 shown in FIGS. 9 to 15, the sample access component and the sample removal paddle or tool are combined into a single and integrally formed sample access and removal component or tool 910. As shown in FIG. 15, the tool 910 is initially an integral part of the housing 900, but is only attached to the remainder of the housing 900 relatively weakly, in this embodiment by way of a small number of breakable joining members 1502. In the illustrated embodiment, the tool 910 somewhat resembles a car key, in that it takes the form of a relatively large paddle tab or handle portion from which extends an elongate engagement portion whose edges are parallel along most of its length, but are inclined towards one another near the end remote from the handle so as to reduce the width of the remote or distal end of the engagement portion, ending with a flat edge orthogonal to the longitudinal axis of the elongate engagement portion. The reduced width of the elongate portion of the tool 910 at its remote end allows it to be easily inserted within the opening formed by the removal of the tool 910 from the housing, since the width of most of that opening is essentially equal to the width of the wider portion of the elongate portion of the tool 910.

As shown in FIG. 13, a user can easily remove the tool 910 from the housing by simply grasping the relatively large handle end of the tool 910, and lifting and/or twisting it away from the other part of the housing 900, thereby breaking the joining members 1502. As shown in FIG. 14, the user can then use the elongate engagement portion of the tool 910 to manually engage the storage component 506 containing the biological components of interest. By sliding the storage component 506 towards the open end of the housing 900, the storage component 506 of the lateral flow strip 500 is separated from the filtering components 502, 504 of the lateral flow strip 500, and can be partially or completely removed from the housing 900, as shown in FIG. 14.

In an alternative embodiment, as shown in the biological sample collection and storage assembly 1600 of FIGS. 16 to 19, a combined sample access and removal component 1602 remains attached to the remainder of the housing by a hinge, and includes a generally cylindrical rotor section 1604 with one or more engagement features projecting therefrom to selectively engage the storage component 506 of the lateral flow strip 500 disposed within the housing.

As the paddle tab or handle portion of the sample access and removal component 1602 in this embodiment is broken away from the remainder of the housing by the user, it rotates on the hinge as a continuation of the breakaway action. This rotation causes the engagement features projecting from the cylindrical rotor section 1604 to contact and frictionally engage the storage component 506 of the lateral flow strip 500. Continued rotation drives the storage component 506 towards the opening in the housing, separating it from the filtering components 502, 504 of the lateral flow strip 500, and driving at least its end out of the housing. With further continued rotation, the engagement features move away from the storage component 506, thereby releasing it so that it is free to drop or otherwise be removed from the assembly. The inner sides of the housing constitute a guide ramp or channel that guides the storage component 506 as it exits the housing such that it will enter a test tube or instrument test aperture for subsequent testing of the sample.

In some alternative embodiments, the housing includes a removable portion and a retaining portion configured for mutual separation, and the removable portion includes a sample engagement component that is operable by a user to selectively engage and release the storage component 506, allowing a user to:

(i) operate the sample engagement component to selectively engage the storage component 506 and thus retain it within the removable portion of the housing;

(ii) separate the removable portion of the housing from the retaining portion of the housing, whereby the storage component remains engaged and is thus retained within the removable portion of the housing and separated from the filtering component(s) which is or are retained within the retaining portion of the housing; and (iii) operate the sample engagement component to selectively release the storage component from the removable portion of the housing for testing or analysis.

For example, in the biological sample collection and storage assembly 2000 shown in FIGS. 20 to 23, the housing consists of two parts: a removable portion 2002 and a retaining portion 2004 that are initially joined by one or more breakable joining members 2008. The removable portion 2002 includes a sample engagement component 2006, in the illustrated embodiment being in the form of a flexible clip. When the clip 2006 is depressed by the user's thumb, the storage component 506 of the lateral flow strip is engaged within the removable portion 2002 of the housing. While maintaining this engagement, the two portions or parts 2002, 2004 of the housing are then separated, in this embodiment by using a 'snap' action or a twisting action as represented by the arrows 2202, 2302 in FIGS. 22 and 23, respectively. To facilitate the snap action, the upper edges of the removable portion 2002 and the retaining portion 2004 are bevelled, which also suggests this action to the user. Either action also separates the storage component 506 of the lateral flow strip from the filtering components 502, 504, while retaining the storage component 506 within the removable portion 2002. The strip substrate or backing sheet 508 is retained within the retaining portion 2004 of the housing, so that only the storage component 506 of the lateral flow strip 500 is retained within the removable portion 2002 of the housing.

The user can then position the engaged storage component 506 of the lateral flow strip 500 over a test tube or test instrument inlet. When the user releases the sample engagement component 2006, the storage component 506 is then safely released into the tube or test instrument for testing without contact by the user, thus reducing the risk of contamination of the user or the sample.

In some embodiments, such as the embodiment shown in FIGS. 24 to 30, the assembly 2400 includes a capillary port or tube 2402 to allow the direct collection of a fluid biological sample into the housing and onto the lateral flow strip 500 therein. The capillary port 2402 constitutes an integrated sample collection device. In use, the capillary port 2402 is brought into contact with a fluid sample, such as a blood droplet, which causes the fluid sample to be drawn into the capillary port 2402 through capillarity action. As shown in the cross-sectional view of FIG. 30, the capillary port 2402 includes a tube that extends through the housing, and the inner end of this tube is in contact with the first filtering component 502 of the lateral flow strip 500 mounted within the housing. This arrangement causes a quantity of the fluid sample to be drawn through the capillary port 2402 and into the lateral flow strip 500, where it is filtered by the filtering components 502, 504, and the remaining components of the biological sample flow to the storage component 506.

In the case of a blood sample, this may be collected from a finger prick blood droplet. A separate lancet such a sterile disposable lancet may be provided together with the biological sample collection and storage assembly to allow the finger prick blood sample to be produced. In some embodiments, the assembly includes an integrated spring loaded sterile lancet (not shown) operable by a user to cause a finger prick and thereby provide a blood sample for receipt by the capillary port 2402.

In some embodiments, the biological sample collection and storage assembly includes a sealed reservoir storing a buffer solution, and a buffer solution release component that is operable by a user to cause release of the buffer solution onto the lateral flow strip 500 after the biological sample to improve flow of the biological sample within the lateral flow strip 500.

For example, the biological sample collection and storage assembly 2400 of FIGS. 24 to 30 includes a sealed reservoir in the form of an integrated wash buffer carried within a small sachet 2404, and includes a buffer solution release component, in the illustrated embodiment being in the form of a deformable moulded button 2406 included as part of the housing. After the sample is collected, this button 2406 is depressed by the user, which presses the sachet 2404 against sharp projections 2408 extending from an inner surface of the housing towards the sachet 2404. Continued pressing by the user eventually ruptures the sachet 2404, allowing the wash buffer to flood the lateral flow strip 500, thereby improving the sample flow through the lateral flow strip 500 and the consequent filtering and sample collection.

In some embodiments, the housing includes a viewing port or inspection window that allows a user to assess correct operation or progress of the collected sample in one or more regions of the lateral flow strip 500, and/or whether the assembly has been prior used. In the described embodiments, the inspection window is a clear plastic insert that is friction or clip retained within the plastic housing. In some embodiments, the clear plastic window includes a lens or other optical feature to improve the visibility of the underlying strip component for visual inspection.

In the embodiment of FIGS. 24 to 30, the housing includes a clear window insert 2410 that allows observation of the strip 500 by the user. This can be used to confirm to correct operation of the device and to identify a used device. In the case of a blood sample collection device, inspection of the red blood cell filter component (e.g., the first filtering component 502) will (or should) show the presence of red blood cells, and any downstream components (e.g., 504, 506) of the lateral flow strip should not show the presence of red blood cells, allowing a user of the assembly to assess whether the correct sample collection and filter action has occurred.

Additionally, where a buffer solution is provided, this solution can include a visible or fluorescent dye to facilitate observation of the progress of the sample flow through the lateral flow strip 500, the successful use and completion of the assembly, and/or prior use of the assembly. Accordingly, the housing can include an inspection window to allow the user to inspect the storage component 506 of the lateral flow strip 500. For example, the wash buffer may contain a blue dye that will not be retained in the filtering components 502, 504, but will pass through the strip assembly mixed with the filtered sample and thus be absorbed onto the storage component 506. In this case, a strong blue colour of the storage component 506 only, visible through at least one appropriately located inspection window will allow the assessment of prior use and correct operation of the device. The dye is selected so as not to interfere with the sample or subsequent tests and to retain its colour when dry.

In some embodiments, an inner surface of the housing supporting the storage component 506 of the lateral flow test strip 500 has a non-planar shape, and an opposing surface of the engagement mechanism has a complementary deforming surface so that when the engagement mechanism is operated the two complementary surfaces press against the storage component 506 and deform it into a non-planar shape corresponding to the shapes of the opposing surfaces. The result is that when the deformed and non-planar storage component 506 is inserted into a test tube, the storage component 506 is located away from the centre of the test tube and generally close to the wall of the test tube, leaving the centre of the test tube accessible for insertion of a pipette or automated sample addition system, for example. Without this feature, a planar storage component 506 tends to block the centre of the test tube, impeding access to the latter.

Figure 31:
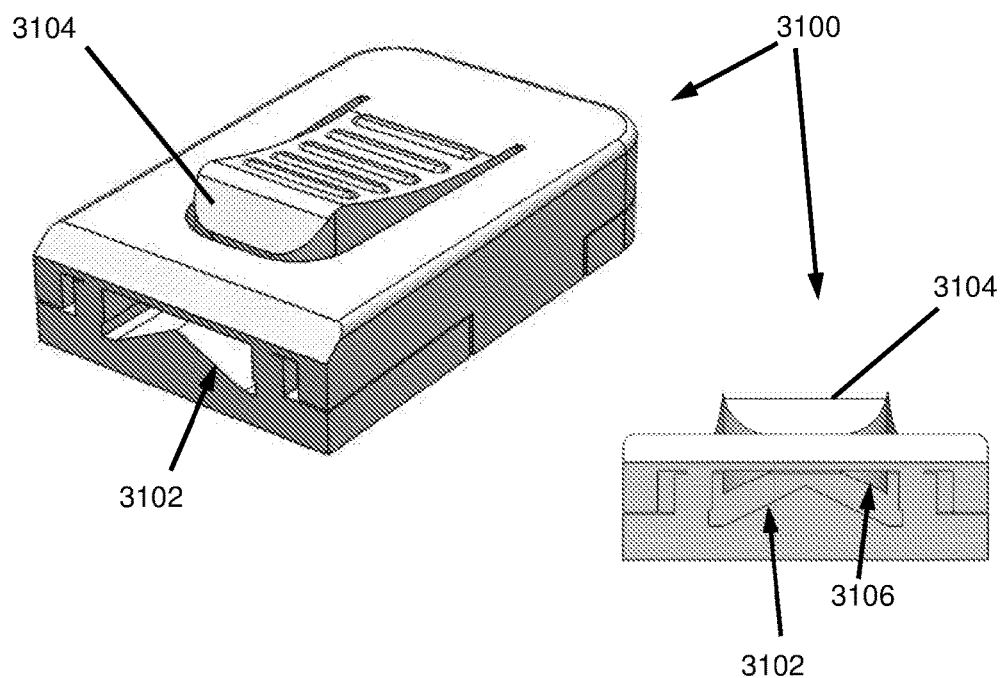
FIGS. 31 to 34 are drawings illustrating the use of deforming features of a housing in accordance with some embodiments of the present invention to deform the storage component of a lateral flow test strip into a non-planar shape so that when the deformed storage component is inserted into a test tube, it does not impede access to the centre of the test tube.
Figure 32:
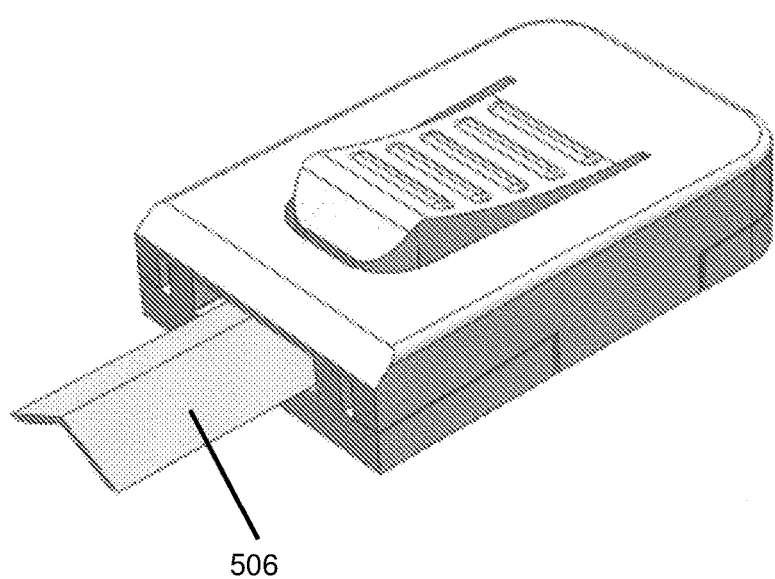

For example, FIGS. 31 to 34 are drawings illustrating the use of deforming features 3402, 3404 of a housing in accordance with further embodiments of the present invention. FIG. 31 shows a retaining portion 3100 having a lower inner (and generally convex) surface 3102 in the form of an extruded V-shape whose apex is parallel to the longitudinal axis of the corresponding biological sample collection and storage assembly. The sample engagement component 3104 of the retaining portion 3100 has a generally concave lower inner surface 3106 of a V-shape complementary to that described above, so that when the sample engagement component 3104 is operated by a user to engage the storage component 506 disposed within the retaining portion 3100, the storage component 506 is pressed between the opposing and complementary V-shaped surfaces 3102, 3106, thereby introducing a fold line along the storage component 506 and permanently deforming the storage component 506 so that it has an extruded V-shape, as shown in FIG. 32.

Figure 33:
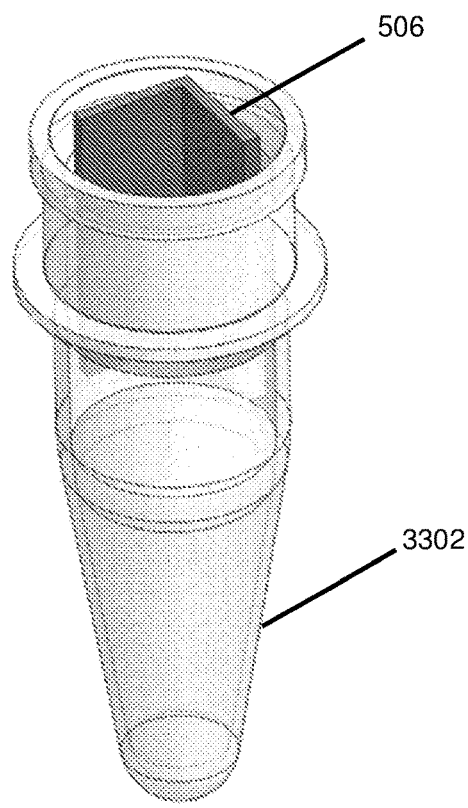
Figure 34:
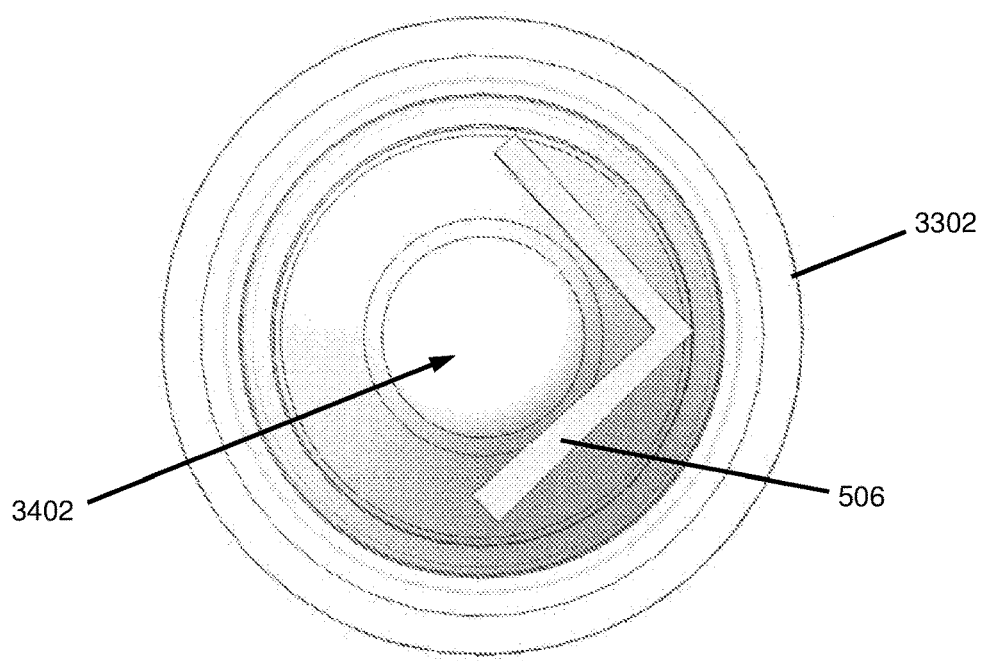

Thus the initially planar storage component 506 of a lateral flow test strip 500 is deformed into a non-planar "V"-shape, as shown in FIG. 32, so that when the V-shaped storage component 506 is inserted into a test tube 3302, as shown in FIG. 33, it does not impede access to the centre 3402 of the test tube 3302, as shown in the plan view of FIG. 34.

Many modifications will be apparent to those skilled in the art without departing from the scope of the present invention.

The invention claimed is:

1. A biological sample collection and storage assembly, including:
   at least one filtering component;
   an absorbent storage component; and
   a housing in which the at least one filtering component and the absorbent storage component are disposed to protect them from contamination, and to protect the external environment and users from contamination from the biological sample within the housing, the housing including a port to receive the biological sample,
   wherein the at least one filtering component is configured to filter a received biological sample in fluid form containing free cells and other biological components to separate the free cells from the other biological components such that the other biological components flow to the absorbent storage component for subsequent testing or analysis, further wherein the assembly is configured to facilitate selective removal of the absorbent storage component for subsequent testing or diagnostic use of the other biological components stored therein, the housing providing a sample removal component operable to selectively engage the absorbent storage component and separate the absorbent storage component from the at least one filtering component, and to subsequently release the absorbent storage component from the assembly for said testing or diagnostic use.

2. The assembly of claim 1, wherein the at least one filtering component includes one or more selective chemical or immunoassay binding components to immobilise the free cells.

3. The assembly of claim 2, wherein the at least one filtering component uses size exclusion to restrict or block the passage of the free cells.

4. The assembly of claim 1, wherein the at least one filtering component uses size exclusion to restrict or block the passage of the free cells.

5. The assembly of claim 1, including a sample receiving component to receive the biological sample in fluid form, wherein the at least one filtering component is disposed between the sample receiving component and the absorbent storage component, and the biological sample flows from the sample receiving component to the absorbent storage component by capillary action.

6. The assembly of claim 5, wherein the sample receiving component, the filtering component, and the absorbent storage component are formed from a single material.

7. The assembly of claim 6, wherein one or more of the at least one filtering component and the absorbent storage component are formed by selective thermal and/or mechanical processing of respective regions of the material.

8. The assembly of claim 1, wherein the at least one filtering component and the absorbent storage component partially overlap such that a flow of fluid between the at least one filtering component and the absorbent storage component occurs by capillary flow through an overlapping portion of the the at least one filtering component to a corresponding overlapping portion of the absorbent storage component.

9. The assembly of claim 1, wherein the at least one filtering component and the absorbent storage component are supported by a common non-absorbent backing layer, and the adhesion of the absorbent storage component to the backing layer is configured to facilitate selective removal of the absorbent storage component.

10. The assembly of claim 1, wherein the sample removal component includes opposing and complementary non-planar mating surfaces configured so that when the sample removal component is operated by a user to engage the absorbent storage component, the absorbent storage component is pressed between the opposing and complementary non-planar surfaces and deformed into a non-planar shape such that when the non-planar absorbent storage component is positioned within a test tube, it is positioned away from the centre of the test tube to allow access to the centre of the test tube.

11. The assembly of claim 10, wherein the at least one filtering component and the absorbent storage component are supported by a common non-absorbent backing layer, and the adhesion of the absorbent storage component to the backing layer is configured to facilitate selective removal of the absorbent storage component.

12. The assembly of claim 10, wherein the housing includes a removable portion and a retaining portion configured for mutual separation, the removable portion including a sample engagement component operable by a user to selectively engage and release the absorbent storage component, such that a user of the assembly can:

(i) operate the sample engagement component to selectively engage the absorbent storage component and thus retain it within the removable portion of the housing;

(ii) separate the removable portion of the housing from the retaining portion of the housing, whereby the absorbable storage component remains engaged and is thus retained within the removable portion of the housing and separated from the at least one filtering component which is retained within the retaining portion of the housing; and (iii) operate the sample engagement component to selectively release the absorbable storage component from the removable portion of the housing for testing or analysis.

13. The assembly of claim 1, wherein the housing includes a removable portion and a retaining portion configured for mutual separation, the removable portion including a sample engagement component operable by a user to selectively engage and release the absorbent storage component, such that a user of the assembly can:

(i) operate the sample engagement component to selectively engage the absorbent storage component and thus retain it within the removable portion of the housing;

(ii) separate the removable portion of the housing from the retaining portion of the housing, whereby the absorbent storage component remains engaged and is thus retained within the removable portion of the housing and separated from the at least one filtering component which is retained within the retaining portion of the housing; and (iii) operate the sample engagement component to selectively release the absorbent storage component from the removable portion of the housing for testing or analysis.

14. The assembly of claim 13, wherein the at least one filtering component and the absorbent storage component are supported by a common non-absorbent backing layer, and the adhesion of the absorbent storage component to the backing layer is configured to facilitate selective removal of the absorbent storage component.

15. The assembly of claim 1, including a sealed reservoir storing a buffer solution, and a buffer solution release component that is operable by a user to cause release of the buffer solution from the sealed reservoir onto the lateral flow strip after the biological sample to improve flow of the biological sample within the lateral flow strip.

16. The assembly of claim 15, wherein the buffer solution includes a visible or fluorescent dye to facilitate observation of the progress of the sample flow through the lateral flow strip, the successful use and completion of the assembly, and/or prior use of the assembly.

17. The assembly of claim 1, wherein the housing includes a viewing port or window that allows a user to assess progress or correct operation of the collected sample in one or more regions of the strip, or whether the assembly has been prior used.

18. The assembly of claim 17, wherein the viewing port or window includes a lens to facilitate the assessment.

19. The assembly of claim 1, including a capillary port to allow direct collection of the fluid biological sample into the housing and onto the lateral flow strip.

20. The assembly of claim 19, including a spring loaded lancet operable by a user to cause a finger prick and thereby provide a blood sample for receipt by the capillary port.

\* \* \* \* \*